(12) United States Patent
Kim

(10) Patent No.: US 10,842,662 B1
(45) Date of Patent: Nov. 24, 2020

(54) PENIS PUMP

(71) Applicant: Ho Yung Kim, Blue Bell, PA (US)

(72) Inventor: Ho Yung Kim, Blue Bell, PA (US)

( * ) Notice: Subject to any disclaimer, the term of this patent is extended or adjusted under 35 U.S.C. 154(b) by 0 days.

(21) Appl. No.: 16/743,667

(22) Filed: Jan. 15, 2020

Related U.S. Application Data

(60) Provisional application No. 62/921,621, filed on Jun. 28, 2019.

(51) Int. Cl.
*A61F 5/41* (2006.01)

(52) U.S. Cl.
CPC .......... *A61F 5/41* (2013.01); *A61F 2005/412* (2013.01)

(58) Field of Classification Search
CPC ....... A61F 5/41; A61F 5/451; A61F 2005/412
USPC ..................................................... 600/38–41
See application file for complete search history.

(56) References Cited

U.S. PATENT DOCUMENTS

| | | |
|---|---|---|
| 4,856,498 A | 8/1989 | Psbon |
| 5,244,453 A | 9/1993 | Osbon |
| 6,036,635 A | 3/2000 | Altshuler |
| 6,193,753 B1 | 2/2001 | Nordheim et al. |
| 6,248,059 B1 | 6/2001 | Gamper et al. |
| 6,309,344 B1 | 10/2001 | Werner |
| 8,382,656 B1 | 2/2013 | Brown |
| 8,622,889 B1 | 1/2014 | Loria |
| 2003/0136415 A1 | 7/2003 | Lanton |
| 2007/0093687 A1 | 4/2007 | Hoefer |
| 2007/0179337 A1 | 8/2007 | Hays |
| 2011/0040142 A1 | 2/2011 | Eum et al. |
| 2011/0213201 A1 | 9/2011 | Moon |
| 2013/0066147 A1 | 3/2013 | Brown |
| 2016/0367430 A1 | 12/2016 | Li |
| 2018/0177625 A1 | 6/2018 | Zhang |
| 2018/0228640 A1 | 8/2018 | Hibri |
| 2019/0133809 A1 | 5/2019 | Jochum |

FOREIGN PATENT DOCUMENTS

| | | |
|---|---|---|
| CN | 2079951 | 7/1991 |
| DE | 4344686 | 10/1996 |
| GB | 2514192 | 11/2014 |

*Primary Examiner* — John P Lacyk
(74) *Attorney, Agent, or Firm* — Joseph E. Maenner; Maenner & Associates, LLC

(57) ABSTRACT

A penis pump includes a hollow cylinder having an open proximal end sized to allow the insertion of a human penis therein and a distal end. A cushion is inserted into the hollow cylinder between the proximal end and the distal end. A support member has a first end connected to the cushion and a second end attached to the distal end.

20 Claims, 2 Drawing Sheets

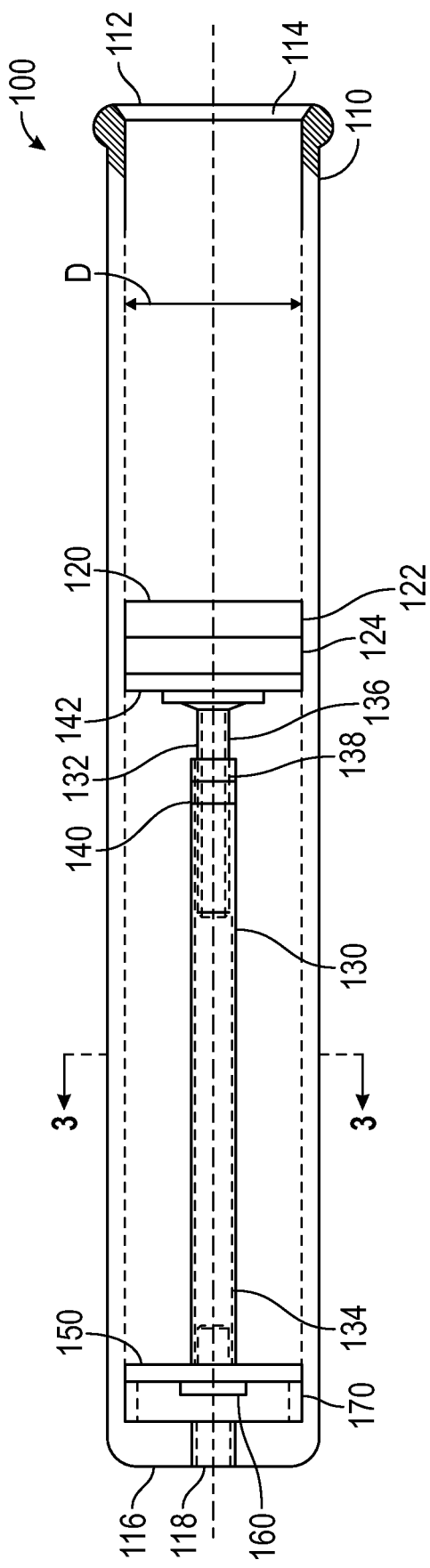
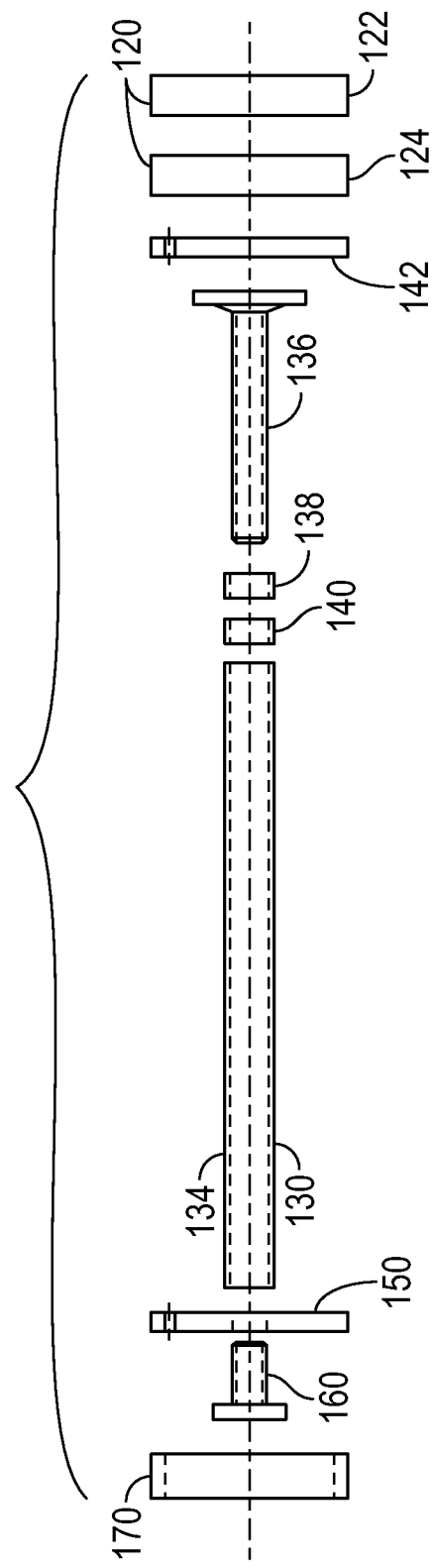

US 10,842,662 B1

PENIS PUMP

CROSS-REFERENCE TO RELATED APPLICATION

This application claims the benefit of U.S. Provisional Patent Application Ser. No. 62/921,621, filed on Jun. 28, 2019, which is incorporated herein by reference in its entirety.

BACKGROUND OF THE INVENTION

Field of the Invention

The present invention relates to pneumatically activated pumps for enlarging a penis.

Description of the Related Art

Penis pumps can be used to apply a vacuum to a penis to enlarge both the length and girth of the penis. Prior art conventional penis pumps, however, can apply too much vacuum too quickly, which can result in temporary bruising, blisters, pinpricks, and other undesired results to the penis.

It would be beneficial to provide a penis pump that slowly applies vacuum to the penis to reduce the risk of damaging or otherwise injuring the penis.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention is a penis pump that includes a hollow cylinder having an open proximal end sized to allow the insertion of a human penis therein and a distal end. A cushion is inserted into the hollow cylinder between the proximal end and the distal end. A support member has a first end connected to the cushion and a second end attached to the distal end.

In an alternative embodiment, the present invention is A penis pump that includes a hollow elongate tube having an open proximal end and a distal end. The distal end has a vacuum pump connection. An axially extendible support rod assembly extends from the distal end toward the proximal end. A compressible material is attached to the support rod assembly.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 1 is a side elevational view, in section of a penis pump according to an exemplary embodiment of the present invention;

FIG. 2 is an exploded side elevational view of the penis pump of FIG. 1, with the external cylinder removed;

DETAILED DESCRIPTION

Figure 3:
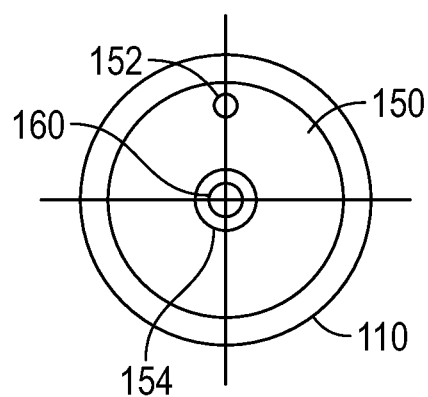
FIG. 3 is a sectional view of the penis pump of FIG. 1, taken along lines 3-3 of FIG. 1.
Figure 4:
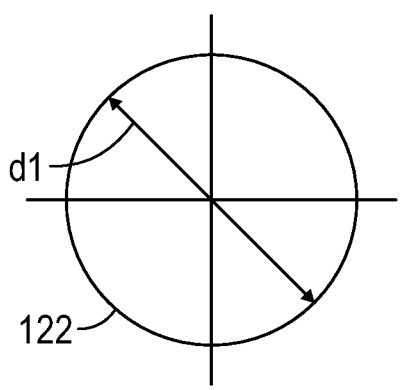
FIG. 4 is a top plan view of a first cushion used with the penis pump of FIG. 1.
Figure 5:
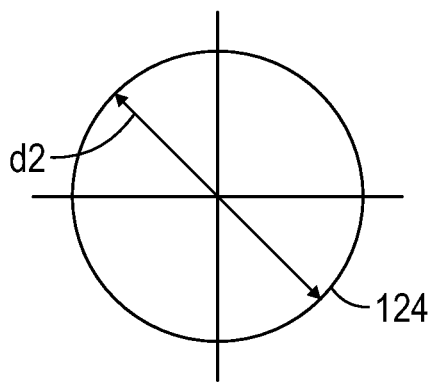
FIG. 5 is a top plan view of a second cushion used with the penis pump of FIG. 1.

In the drawings, like numerals indicate like elements throughout. Certain terminology is used herein for convenience only and is not to be taken as a limitation on the present invention. The terminology includes the words specifically mentioned, derivatives thereof and words of similar import. As used herein, the term "proximal" means a location closer to the penis insertion end of the invention and the term "distal" means a direction farther from the penis insertion end of the invention.

The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

The word "about" is used herein to include a value of +/−10 percent of the numerical value modified by the word "about" and the word "generally" is used herein to mean "without regard to particulars or exceptions."

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

The present invention provides a penis pump that can be used to enlarge the length and girth of a human penis, as well as to allow a user to masturbate while his penis is inserted in the pump.

Referring to the Figures, a penis pump 100 includes a hollow cylinder 110 (shown in FIG. 1) into which a penis can be inserted. Cylinder 110 can be constructed from a transparent polymer, such as acrylic. Optionally, cylinder 110 can include graduated indicia extending from a proximal end to indicate the length of a penis inserted into cylinder 110. Cylinder 110 can be provided in different lengths and different internal diameters to accommodate different size penises.

Cylinder 110 has an open proximal end 112 that is sized to allow the insertion of a human penis therein. Optionally, an elastic sleeve 114 can be inserted over proximal end 112. Sleeve 114 has a central through opening that allows a penis to be inserted therethrough. The through opening is smaller than the width of an erect penis so that sleeve 114 forms a seal around the erect penis. Alternatively, sleeve 114 can be omitted and a cylinder 110 that is narrow enough to form a seal between cylinder 110 and a user's penis, without a sleeve, can be used.

Cylinder 110 also includes a distal end 116 that is generally closed, but with a pump connection opening 118 for a vacuum pump (not shown). In an exemplary embodiment, opening 118 can be a ⅜"-18 threaded opening to connect to a vacuum pump. Cylinder 110 includes a generally constant internal diameter "D" extending between proximal end 112 and distal end 116. In an exemplary embodiment, "D" is about 1½ inches.

Referring to FIGS. 1, 2, 4, and 5 cushion 120 is inserted into hollow cylinder 110 between proximal end 112 and distal end 116. Cushion 120 is constructed from an air permeable material, such as open cell foam, and includes a first cushion 122 having a first durometer and a second cushion 124, distal from first cushion 122, and having a second durometer, harder than the first durometer. In an exemplary embodiment, each cushion 122, 124 can be about ¼ inch thick. First cushion 122 can have a first diameter "d1" that is smaller than "D" and second cushion 124 can have a diameter "d2" that is larger than "D". For a "D" of 1½ inches, "d1" can be about 1.49 inches and "d2" can be about 1.6 inches. The diameter "d2" of second cushion 124 being larger than "D" of cylinder 110 allows second cushion 124 to extend across the entire internal diameter of cylinder 110. First cushion 122 can freely float within cylinder 110.

An axially extendible support member 130, shown in FIGS. 1 and 2, has a first, proximal end 132 connected to cushion 120 and a second, distal end 134 attached to distal end 116 of cylinder 110. Axially extendible support member 130 can include a distal portion 134 and a proximal portion 136 threadingly engaged with distal portion 134. The threaded connection between distal portion 134 and proximal portion 136 allows support member to be axially extended or contracted by rotating and threading proximal portion 136 with respect to distal portion 134. In an exemplary embodiment, distal portion 134 can be a ¼ inch internal diameter plastic pipe and proximal portion 136 can be ¼"-20×2 inch stainless steel. Two ¼"-20 stainless steel lock nuts 138, 140 can be threaded onto proximal portion 136 so that, when the relative positions of distal portion 134 and proximal portion 136 are set, lock nuts 138, 140 can be locked down to prevent rotation of proximal portion 136 with respect to distal portion 134.

Figure 6:
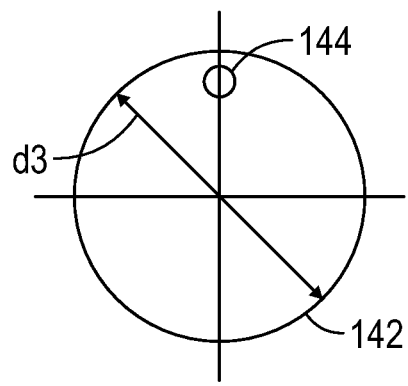
FIG. 6 is a top plan view of a proximal disc used with the penis pump of FIG. 1.
Figure 7:
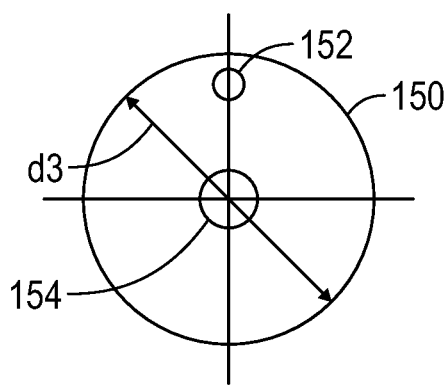
FIG. 7 is a top plan view of a distal disc used with the penis pump of FIG. 1.

A proximal disc 142, shown in FIGS. 1, 2, and 6, is located between proximal end 132 of support member 130 and cushion 120. In an exemplary embodiment, proximal disc 142 can be 1/16 inch thick acrylic having a diameter "d3" of less than "D" or, in a specific embodiment, about 1.49 inches. Proximal disc 142 provides support for cushion 120. Proximal disc 142 comprises a through opening 144 located proximate to a perimeter of proximal disc 142. Through opening 144 can have a diameter of about 0.118 inches and is provided to allow for the passage of air from one side of proximal disc 142 to the opposite side of proximal disc 142.

Proximal disc 142 can be adhered to cushion 120, specifically second cushion 124 by an adhesive and proximal disc 142 can also be adhered to proximal portion 136 of support member 130 with an adhesive or, alternatively, with a bolt (not shown) extending through proximal disc 142 and into proximal portion 136 of support member 130.

A distal disc 150, shown in FIGS. 1, 2, 3, and 7, is attached to distal end 134 of support member 130. In an exemplary embodiment, distal disc 150 can be 1/16 inch thick acrylic having a diameter "d3" of less than "D" or, in a specific embodiment, about 1.49 inches. Distal disc 150 spaces support member 130 away from vacuum pump connection opening 118 at distal end 116 of cylinder 110. Distal disc 150 comprises a through opening 152 located proximate to a perimeter of distal disc 150. Through opening 152 can have a diameter of about 0.118 inches and is provided to allow for the passage of air from one side of distal disc 150 to the opposite side of distal disc 150.

Distal disc 150 also includes a central through opening 154 sized to allow a bolt to extend therethrough. In an exemplary embodiment, central through opening 154 has a diameter of about ¼ inch.

A screw 160, shown in FIGS. 1-3, extends through central through opening 154 and into distal end 134 of support member 130 to secure distal disc 150 to support member 130 so that support member 130 extends from distal end 116 of cylinder toward proximal end 112 of cylinder 110. In an exemplary embodiment, screw 160 can be ¼"-20×⅜" stainless steel.

Figure 8:
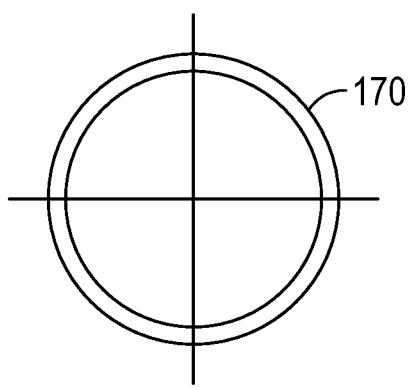
FIG. 8 is a top plan view of a spacer used with the penis pump of FIG. 1.

A spacer ring 170, shown in FIGS. 1, 2, and 8, is disposed distal of distal disc 150, between distal disc 150 and distal end 116 of cylinder 110. Spacer ring 170 can be an annular ring 1/16 inch thick and 0.400 inches in length. Spacer ring 170 engages distal disc 150 to space distal disc 150 away from distal end 116 of cylinder 110. It is important that through opening 154 in distal disc 150 is sufficiently close to the center of distal disc 150 so that ring 170 does not block through opening 154. Spacer ring 170 also spaces the head of screw 160 away from pump connection opening 118.

To use pump 100, a user then can apply a lubricant (not shown) to his penis (not shown) and insert his penis into proximal end 112 of cylinder 110. The distance between first cushion 122 and proximal end 112 can be adjusted by adjusting the insertion length of proximal portion 136 of support member 130 with respect to distal portion 134 of support member 130. It is desired to adjust the distance between first cushion 122 and proximal end 112 so that the tip of the penis engages first cushion 122.

The user can then reciprocate pump 100 with respect to the penis by either moving pump 100 with respect to the penis or moving the penis with respect to pump 100 to simulate a sexual act. Engagement of the tip of the penis with first cushion 122 can provide a pleasurable sensation.

Additionally or alternatively, a user can attach a vacuum pump (not shown) to vacuum pump connection 118. The user can turn on the vacuum pump, which will suck air out of cylinder 110. Sleeve 114 around proximal end 112 of cylinder 110 will prevent ambient air from being drawn into cylinder 110 while air inside cylinder 110 is drawn out by the vacuum. Through openings 144, 152 in proximal disc 142 and distal disc 150, respectively, are sufficiently small to allow air to flow though them, but relatively slowly in order to prevent excess stress on the penis. As air is drawn from cylinder 110, the penis can expand in length and girth.

While pump 100 is envisioned primarily for use with a penis, pump 100 can also be applied over a breast/nipple to enlarge the breast and/or nipple and to provide a pleasurable sensation to the breast/nipple.

Pump 100 is believed to provide medical benefits to a user, which can include a decrease in the likelihood of prostate cancer; an increase in blood circulation in the penis and in the user's body as a whole; an elongation of the sexual life of the user; and provide the user with a more pleasurable life.

It will be further understood that various changes in the details, materials, and arrangements of the parts which have been described and illustrated in order to explain the nature of this invention may be made by those skilled in the art without departing from the scope of the invention as expressed in the following claims.

I claim:

1. A penis pump comprising:
   a hollow cylinder having an open proximal end sized to allow the insertion of a human penis therein and a distal end;
   a cushion inserted into the hollow cylinder between the proximal end and the distal end; and
   a support member having a first end connected to the cushion and a second end attached to the distal end.

2. The penis pump according to claim 1, wherein the distal end of the hollow cylinder comprises a pump connection opening.

3. The penis pump according to claim 1, wherein the cushion comprises an air permeable material.

4. The penis pump according to claim 1, wherein the support member is axially extendible.

5. The penis pump according to claim 4, wherein the support member comprises a distal portion and a proximal portion threadingly engaged with the distal portion.

6. The penis pump according to claim 1, further comprising a proximal disc between the first end of the support member and the cushion.

7. The penis pump according to claim 6, wherein the proximal disc comprises a through opening located proximate to a perimeter of the proximal disc.

8. The penis pump according to claim 1, further comprising a distal disc attached to the second end of the support member.

9. The penis pump according to claim 8, wherein the distal disc comprises a through opening located proximate to a perimeter of the distal disc.

10. The penis pump according to claim 8, further comprising a spacer ring distal of the distal disc.

11. A penis pump comprising:
    a hollow elongate tube having an open proximal end and a distal end, the distal end having a vacuum pump connection;
    an axially extendible support rod assembly extending from the distal end toward the proximal end; and
    a compressible material attached to the support rod assembly.

12. The penis pump according to claim 11, wherein the elongate tube has an internal diameter and wherein the compressible material extends across the internal diameter.

13. The penis pump according to claim 11, wherein the compressible material comprises an air permeable material.

14. The penis pump according to claim 11, wherein the support rod assembly is spaced from the vacuum pump connection.

15. The penis pump according to claim 11, further comprising a distal disc attached to a distal end of the support rod assembly.

16. The penis pump according to claim 15, wherein the distal disc has central opening and a distal through opening formed therein, distal from the central opening.

17. The penis pump according to claim 11, further comprising a proximal disc attached to a proximal end of the support rod assembly.

18. The penis pump according to claim 17, wherein the proximal disc a proximal through opening formed therein.

19. The penis pump according to claim 11, wherein the compressible material comprises a first cushion having a first durometer and a second cushion, distal from the first cushion, and having a second durometer, harder than the first durometer.

20. The penis pump according to claim 11, wherein the open proximal end of the cylinder comprises an elastic sleeve.

* * * * *